United States Patent
Choi et al.

(10) Patent No.: US 10,481,148 B2
(45) Date of Patent: Nov. 19, 2019

(54) CELL LINE STABLY EXPRESSING NAV1.5 AND METHOD OF SCREENING THERAPEUTIC AGENT USING THE CELL LINE

(71) Applicant: THE CATHOLIC UNIVERSITY OF KOREA INDUSTRY-ACADEMIC COOPERATION FOUNDATION, Seoul (KR)

(72) Inventors: Jin-Sung Choi, Seoul (KR); Jeong Hee Choi, Cheongju-si (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 202 days.

(21) Appl. No.: 15/444,335

(22) Filed: Feb. 28, 2017

(65) Prior Publication Data

US 2018/0080924 A1    Mar. 22, 2018

(30) Foreign Application Priority Data

Sep. 22, 2016  (KR) .................. 10-2016-0121472

(51) Int. Cl.
| | | |
|---|---|---|
| A61K 35/12 | (2015.01) | |
| G01N 33/50 | (2006.01) | |
| C07K 14/705 | (2006.01) | |
| G01N 33/487 | (2006.01) | |
| G01N 33/68 | (2006.01) | |

(52) U.S. Cl.
CPC ....... G01N 33/5014 (2013.01); C07K 14/705 (2013.01); G01N 33/48728 (2013.01); G01N 33/6872 (2013.01); G01N 2333/705 (2013.01); G01N 2500/04 (2013.01); G01N 2500/10 (2013.01)

(58) Field of Classification Search
None
See application file for complete search history.

(56) References Cited

U.S. PATENT DOCUMENTS

| | | | | |
|---|---|---|---|---|
| 7,087,374 | B2 * | 8/2006 | Wang .................. | C07K 14/705 435/4 |
| 7,485,455 | B2 * | 2/2009 | Makielski ............ | C07K 14/705 435/320.1 |
| 2011/0312533 | A1 | 12/2011 | Shekdar et al. | |

FOREIGN PATENT DOCUMENTS

| | | |
|---|---|---|
| WO | 03/080570 A2 | 10/2003 |
| WO | 2010/071983 A1 | 7/2010 |
| WO | 2016/026732 A1 | 2/2016 |

OTHER PUBLICATIONS

Liu et al., Recombinase-Mediated Cassette Exchange to Rapidly and Efficiently Generate Mice With Human Cardiac Sodium Channels. Genesis, 2006, 44:556-564 (Year: 2006).*
Nagatomo et al., Temperature dependence of early and late currents in human cardiac wild-type and long Q-T DKPQ Na+ channels. Am. J. Physiol. 275 (Heart Circ. Physiol. 44): H2016-H2024, 1998. (Year: 1998).*
De la Luna et al., pac gene as efficient dominant marker and reporter gene in mammalian cells. Methods Enzymol. 1992;216:376-85. (Year: 1992).*
NCBI Reference Sequence: NM_198056.2. Homo sapiens sodium voltage-gated channel alpha subunit 5 (SCN5A), transcript variant 1, mRNA. pp. 1-14. (Year: 1992).*
Martin B. Rook et al., "Biology of cardiac sodium channel Nav1.5 expression", Cardiovascular Research (2012) 93, 12-23.
Gül Erdemli et al., "Cardiac safety implications of hNav1.5 blockade and a framework for pre-clinical evaluation", frontier in Pharmacology, Jan. 2012, vol. 3, Article 6.
Jia Lu, PhD et al, "Improving cardiac conduction with a skeletal muscle sodium channel by gene and cell therapy", J Cardiovasc Pharmacol., Jul. 2012, 60(1): 88-99.

* cited by examiner

Primary Examiner — Christopher M Babic
Assistant Examiner — Arthur S Leonard
(74) Attorney, Agent, or Firm — Revolution IP, PLLC

(57) ABSTRACT

Provided are a cell line stably expressing voltage-gated sodium channel (Nav1.5), wherein a SCN5A gene (NCBI accession no. NM_198056) encoding Nav1.5 and a puromycin selection marker are inserted into a chromosome of a host cell, and a method of measuring cardiotoxicity of a test substance comprising: (1) contacting a test substance to the cell line of claim 1; and (2) measuring magnitude of voltage-gated sodium channel (Nav1.5) in the cell line in contact with the test substance.

5 Claims, 3 Drawing Sheets

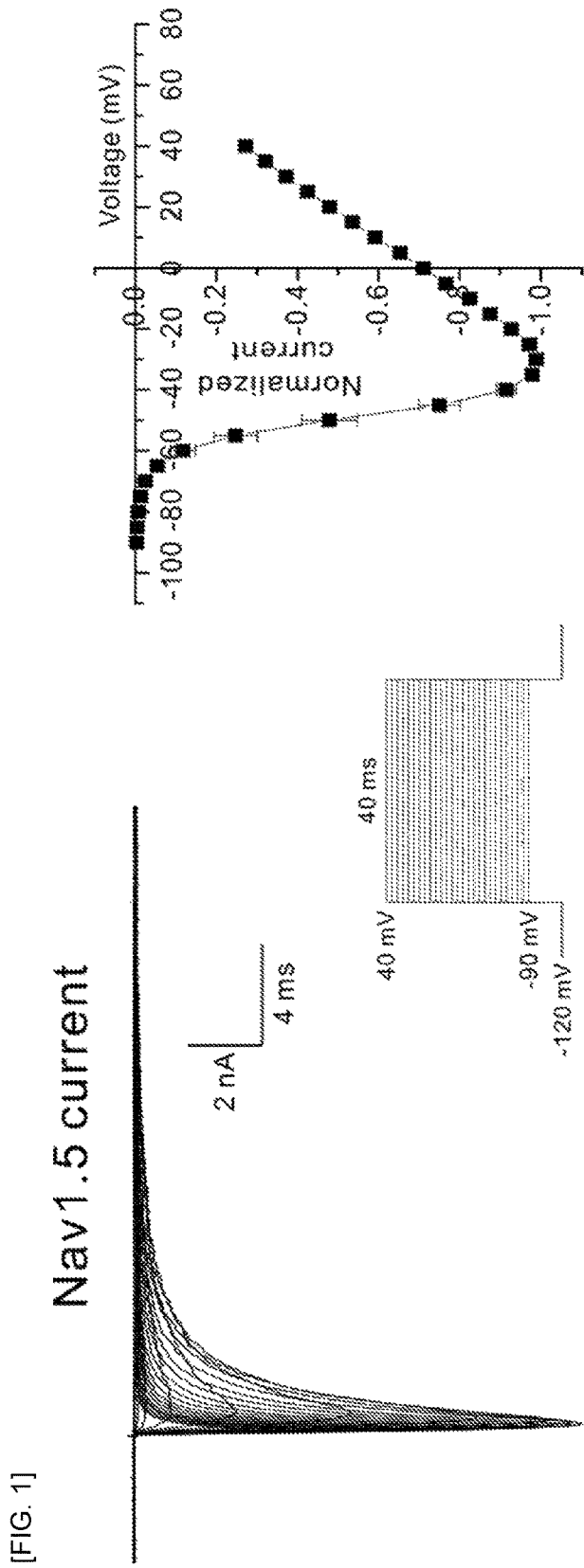
[FIG. 1]

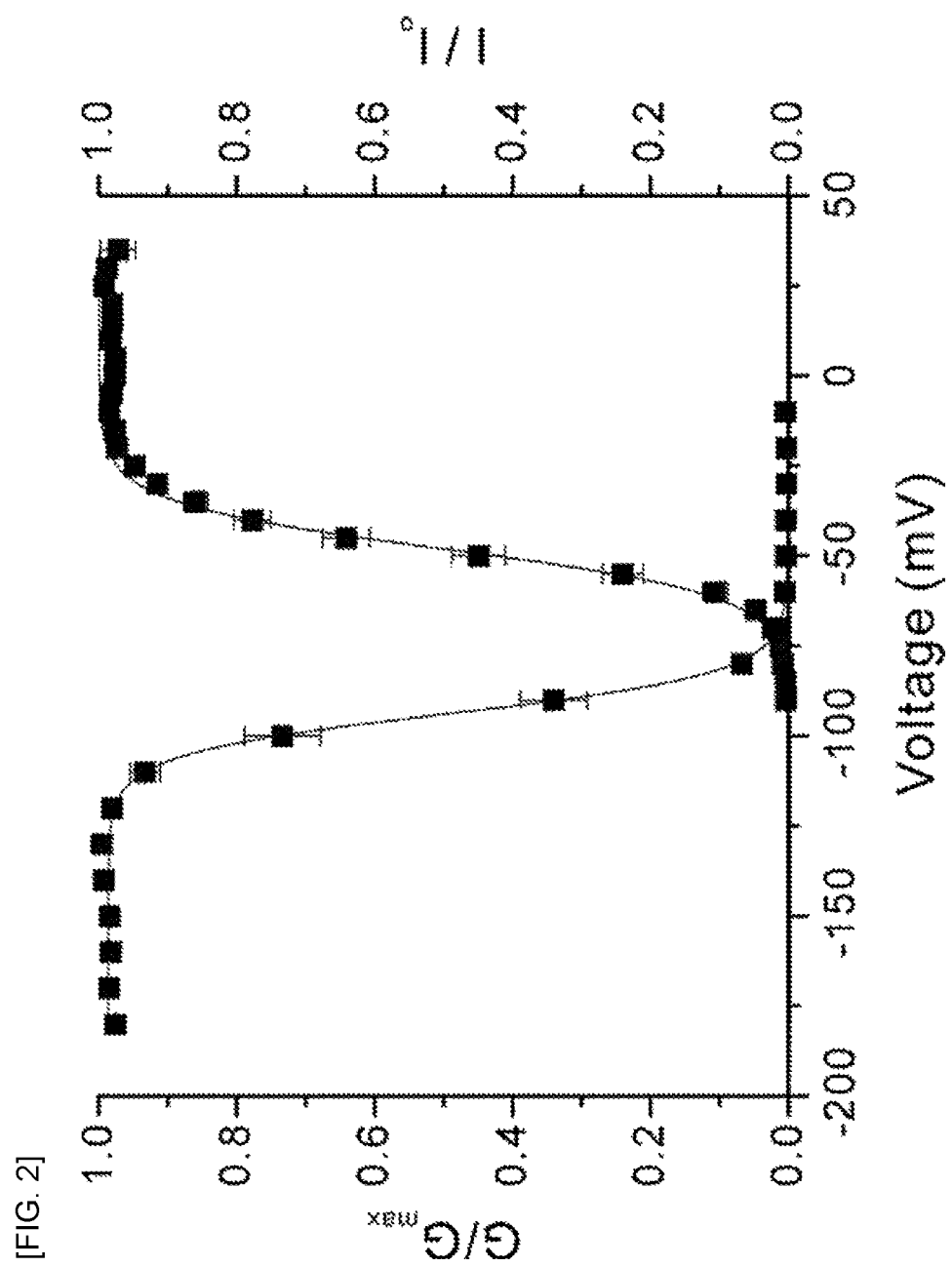
[FIG. 2]

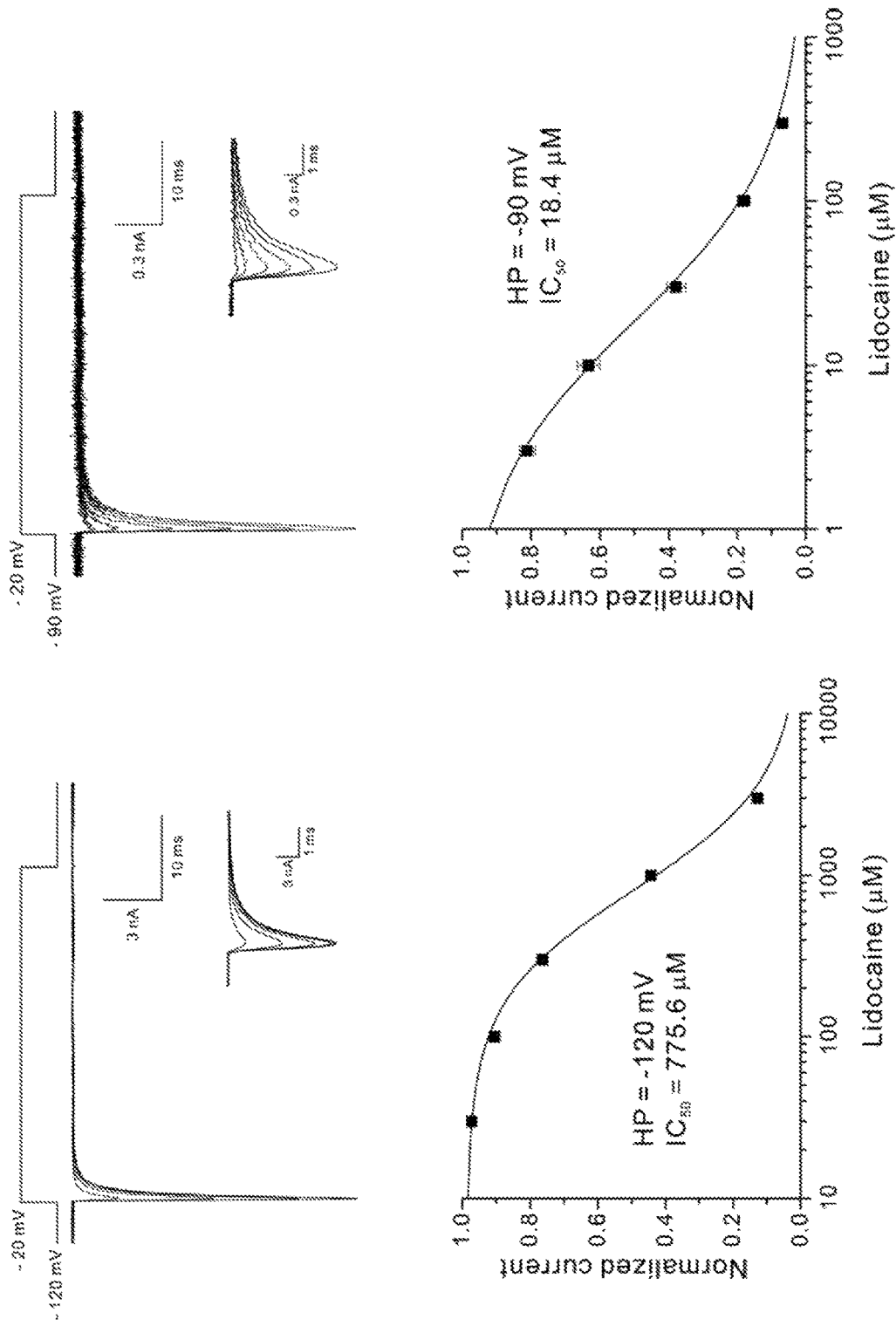
[FIG. 3]

CELL LINE STABLY EXPRESSING NAV1.5 AND METHOD OF SCREENING THERAPEUTIC AGENT USING THE CELL LINE

CROSS-REFERENCE TO RELATED APPLICATION

This application claims the benefit of Korean Patent Application No. 10-2016-0121472, filed on Sep. 22, 2016, in the Korean Intellectual Property Office, the disclosure of which is incorporated herein in its entirety by reference.

BACKGROUND

1. Field

The present disclosure relates to a cell line that stably expresses human voltage-gated sodium channel (Nav1.5) (description: *Homo sapiens* sodium channel, voltage-gated, type V, alpha subunit (SCN5A), transcript variant 1), which is a expressed in cardiac muscle of humans, and a method of screening a therapeutic agent using the cell line.

2. Description of the Related Art

Many drugs that cause cardiovascular diseases have been found to be a major part among drugs that have been withdrawn over the last 15 years, and accordingly, the need for safety pharmacology tests for cardiovascular diseases has been raised. The ultimate competitiveness of most therapeutic agents discovered in the development of new drugs depends on the 'safety' for humans. However, currently, many therapeutic agents are found to have side effects such as ventricular repolarization and arrhythmia. In particular, cardiac toxicity which is acute toxicity is a very important safety factor, and thus the safety thereof in humans is predicted through animal experiments in the non-clinical state of the development of new drugs. However, ethical problems of animal experiments have to be considered in the case of the toxicity test using animals, and results obtained from the toxicity test using animals may be different from the safety for humans. Recently, rather than experimental animals, cell lines expressing main proteins in humans are used to measure drug safety.

In the development of a therapeutic agent, suppression of Nav1.5 current by a new drug may cause side effects such as acute heart attack, and thus, the degree of suppression of the current may be measured. However, if the magnitude of the current is small, the ratio of signal-to-noise (S/N) is lowered due to experimental errors such as leak current or noise, and accordingly, the reliability of the measured value is also lowered. Therefore, as long as the magnitude of the current does not exceed a maximum effective range that the experimental machine can measure, the larger magnitude the current produced by a cell line has, the higher the S/N ratio is, so that the more reliable experimental data can be obtained. However, a cell line having a sufficiently large current magnitude of $Na_v1.5$ has not yet been developed.

DOCUMENT IN RELATED ARTS

Patent Document

WO 2010/071983 (published on Jul. 1, 2010)

SUMMARY

Provided is a cell line stably expressing human voltage-gated sodium channel (Nav1.5).

Provided is a method of measuring cardiotoxicity by measuring magnitude of $Na_v1.5$ current in the cell line.

Provided is a method of screening an inhibitor for cardiotoxicity by measuring magnitude of Nav1.5 current in the cell line.

Additional aspects will be set forth in part in the description which follows and, in part, will be apparent from the description, or may be learned by practice of the presented embodiments.

In an embodiment, there is provided a cell line stably expressing human voltage-gated sodium channel (Nav1.5), the cell line being produced in a way that a SCN5A gene (NCBI accession no. NM_198056) encoding Nav1.5 and a puromycin selection marker are inserted into a chromosome of a host cell.

In an embodiment, there is provided a method of measuring cardiotoxicity of a test substance, the method including: (1) contacting a test substance to a cell line; and (2) measuring magnitude of Nav1.5 current in the cell line in contact with the test substance.

In an embodiment, there is provided a method of screening an inhibitor for cardiotoxicity, the method including: (1) contacting a test substance to a cell line; (2) measuring magnitude of Nav1.5 current in the cell line in contact with the test substance; and (3) selecting the test substance having increased magnitude of Nav1.5 current as compared to magnitude of Nav1.5 current in a control sample.

BRIEF DESCRIPTION OF THE DRAWING

These and/or other aspects will become apparent and more readily appreciated from the following description of the example embodiments, taken in conjunction with the accompanying drawing in which:

FIG. 1 shows graphs each showing hNav1.5 current and current-voltage curve;

FIG. 2 is a graph showing voltage-dependent activation curve and steady state voltage-dependent inactivation curve; and FIG. 3 shows graphs each showing inhibitory results of hNav1.5 current by lidocaine at a holding potential (HP) of −120 mV and −90 mV.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

An embodiment of the present inventive concept provides a cell line stably expressing human voltage-gated sodium channel (Nav1.5), the cell line being produced in a way that a SCN5A gene (NCBI accession no. NM_198056) encoding Nav1.5 and a puromycin selection marker are inserted into a chromosome of a host cell.

In an embodiment, the cell line stably expressing Nav1.5 may have accession number KCTC 13095BP, but embodiments are not limited thereto.

In an embodiment, the cell line stably expressing Nav1.5 may have current magnitude in a range from about 5.5 nA to about 19.6 nA, and may have average current quantity of about 8.8±0.8 nA. However, embodiments are not limited thereto.

In an embodiment, the host cell may be a human embryonic kidney 293 (HEK293) cell, but embodiments are not limited thereto.

The term "SCN5A gene encoding Nav1.5" as used herein may refer to transcript variant 1 (Q1077; NM_198056) among a total of 6 SCN5A transcript variants, and may be the longest variant that is translated into 1,406 amino acids and cases no mutations (mRNA Refseq: NM_198056.1, Protein Refseq: NP_932173).

An embodiment of the present inventive concept provides a measuring cardiotoxicity of a test substance, the method including: (1) contacting a test substance to a cell line; and (2) measuring magnitude of Nav1.5 current in the cell line in contact with the test substance.

An embodiment of the present inventive concept provides a method of screening an inhibitor for cardiotoxicity, the method including: (1) contacting a test substance to a cell line; (2) measuring magnitude of Nav1.5 current in the cell line in contact with the test substance; and (3) selecting the test substance having increased magnitude of Nav1.5 current as compared to magnitude of Nav1.5 current in a control sample.

The term "test substance" as used herein in connection with the screening method may refer to an unknown candidate substance used in the screening method to determine whether the unknown candidate substance influences magnitude of Nav1.5 current. The test substance may include a compound, a nucleotide, an antisense-RNA, a small interference RNA (siRNA), and a natural extract, but embodiments are not limited thereto.

Hereinafter, to promote understanding of one or more embodiments, the inventive concept will be described more fully with reference to Examples below. However, Examples shown and described herein are illustrative examples of the inventive concept and are not intended to otherwise limit the scope of the inventive concept in any way. These Examples are provided so that this disclosure will be thorough and complete, and will fully convey the concept of the inventive concept to those skilled in the art.

<Example> Manufacture of Cell Line Stably Expressing Nav1.5

1. Manufacture of Stable Cell Line

To manufacture HEK293 cell line that stably expresses human Nav1.5 (hNav1.5), a plasmid including a SCN5A gene (transcript variant 1; Q1077; NM_198056) that encodes hNav1.5 was purchased from OriGene Technologies, Inc., and then, was subjected to PCR amplification. The amplified genes were sub-cloned into pSF-CMV-puro vector (available from Sigma), and then, transfected with HEK293 cells. Puromycin was applied thereto for 3 weeks in terms of selection and induction of SCN5A stable cell line derived from a single cell. Among cell lines that stably express Nav1.5 current, electrophysiological techniques were used to screen and establish a cell line of which biophysical characteristics of Nav1.5 current are the same as those of hNav1.5 current that has been temporarily expressed.

2. Electrophysiology

For electrophysiological analysis of hNav1.5 current, current was measured by using Axopatch 200B (manufactured by Molecular Devices Company) and Patchliner Octo (manufactured by Nanion Company) for the manual patch-clamp recording and the automated patch-clamp recording, respectively. Here, the composition (mM) of the extracellular fluid used herein included 140 NaCl, 3 KCl, 1 $CaCl_2$, 1 $MgCl_2$, and 10 HEPES (pH 7.3, NaOH), and the composition (mM) of the intracellular fluid included 140 CsF, 1 EGTA, 10 NaCl, and 10 HEPES (pH 7.3, CsOH).

(1) Manual Patch-Clamp Recording Method

A glass electrode having a resistance value in a range from about 0.7 MΩ to about 1.5 MΩ in the case of addition of the intracellular fluid using a horizontal microelectrode puller was prepared. Then, the glass electrode was adhered to a cell through whole-cell configuration, thereby recording hNav1.5 current. hNav1.5 current data were stored in a computer through Digidata 1440A interface. A pClamp 10.5 software was used to record and analyze data. To minimize the distortion of the recorded hNav1.5 current, only cells having a series resistance of about 1.5 MΩ or less during the whole-cell configuration were used. If the current was greater than about 5 nA, 80% of the series resistance was compensated. The recording of current was started 5 minutes after the whole-cell configuration was used, so as to obtain stable current. Here, liquid junction potential was not corrected. To verify pharmacological effects of lidocaine, extracellular fluid or extracellular fluid containing lidocaine at various concentrations was continuously perfused and recorded using a perfusion pencil.

(2) Automated Patch-Clamp Recording Method

NPC®-16 chips having low resistance (about 1.5 MΩ to about 2.0) were placed on NPC-16 Patchliner Octo platform (Nanion Technologies GmbH) using two EPC 10 quadro patch-clamp amplifiers to measure and record hNav1.5 current from the cells. Here, current was automatically recorded by using a PatchControlHT software, and the recorded current was analyzed by using a Patchmaster software.

3. Biophysical Characteristics hNav1.5 Current

First, to accurately identify biophysical characteristics of hNav1.5 current, the manual patch-clamp recording method was used. To measure the maximum current that cells can generate, a holding potential was set to about −120 mV, and the cells were depolarized at an interval of about 5 mV from about −90 mV to about +40 mV for 40 ms every 10 seconds. Then, current generated in the cells undergone the stimulation was recorded (see FIG. 1). In all the cells being measured (n=12), the current was generated in a range from a minimum of about 5.5 nA to a maximum of about 19.6 nA, and average current quantity of the cells was about 8.8±0.8 nA. To eliminate the difference in the current quantity depending on the cell size, the measured current quantity was divided by unit area of the cells (i.e., capacitance of the cells), to thereby measure current density. The current density measured herein was about 319 pA/pF at a minimum and about 921 pA/pF at a maximum, and the average current density was about 556±45 pA/pF. To determine the current quantity of the cells at each voltage, a current-voltage curve (see right of FIG. 1) was plotted, and accordingly, it was found that maximum current appeared at a voltage of about −30 mV and reversal potential appeared at a voltage of about +57.7 mV, in a similar manner as in the equilibrium potential of sodium current.

The voltage-dependant activation curve (see left of FIG. 1) was optimized according to the Boltzmann distribution below, and more particularly, reversal potential obtained from the current-voltage curve was used to calculate conductance (G) which was to be divided by a maximum value:

$$G = \frac{G_{max}}{1+e^{\frac{V_{50}-V}{k}}}$$

Here, $V_{50}$ indicates voltage that is 50% of a maximum value, and $V_{50}$ of Nav1.5 current of about −47.15±0.59 mV.

The steady state voltage-dependent inactivation curve (see right axis of FIG. 2) was optimized according to the Boltzmann distribution below, and more particularly, current generated at −10 mV for 40 ms after applying stimulation thereto with voltage increased by 10 mV from about −180 mV to about −10 mV for 500 ms every 10 seconds at holding potential of about −120 mV was divided by a maximum value:

$$\frac{I}{I_0} = \frac{1}{1+e^{\frac{V_{50}-V}{k}}}$$

Here, $V_{50}$ voltage that is 50% of a maximum value, and $V_{50}$ of hNav1.5 current in the steady state voltage-dependent inactivation curve was about −92.80±4.53 mV.

To measure inhibitory effects of lidocaine on hNav1.5 current, the cells were depolarized at an interval of −20 mV for 40 ms every 5 seconds at holding potential of about −120 mV where hNav1.5 current was not inactivated (upper left of FIG. 3) and at holding potential of about −90 mV which is a similar level with stable potential of the cardiac muscle (see right upper of FIG. 3), thereby recording hNav1.5 current. Here, the flow of lidocaine at various concentrations was added to the cells, to thereby measure the degree to which the peak of the current was inhibited. The magnitude of the inhibited current was optimized according to the Hill equation, and then, the concentration of lidocaine at which the current was inhibited by 50% was calculated. Consequently, it was found that the concentration at which inhibition of hNav1.5 current by lidocaine appeared was about 775.64±37.10 μM at −120 mV (see left bottom of FIG. 3) and about 18.42±2.60 μM at −90 mV (see right bottom of FIG. 3).

[Accession Number]

Name of depository institution: Korean Research Instituted of Bioscience and Biotechnology Accession number: KCTC 13095BP (Receipt of microorganism deposit is appended to this disclosure)

Accession date: Sep. 1, 2016

According to one or more embodiments of the present inventive concept, a cell line stably expressing Nav1.5 and a method of screening a therapeutic agent using the cell line are disclosed. The inventors of the present inventive concept developed a new cell line in a way that hNav1.5, which is a sodium channel mainly expressed in human cardiomyocytes, was stably expressed in a human embryonic kidney 293 (HEK293) cell. Here, the new cell line was developed by using automated electrophysiological devices as well as traditional electrophysiological techniques, to thereby measure toxicity of drugs. Therefore, the cell line of the present inventive concept can be effectively utilized for screening cardiotoxicity of pharmaceutical products.

It should be understood that the example embodiments described herein should be considered in a descriptive sense only and not for purposes of limitation. Descriptions of features or aspects within each example embodiment should typically be considered as available for other similar features or aspects in other embodiments.

While one or more example embodiments have been described with reference to the figures, it will be understood by those of ordinary skill in the art that various changes in form and details may be made therein without departing from the spirit and scope as defined by the following claims.

What is claimed is:

1. A cell line stably expressing voltage-gated sodium channel (Nav1.5), the cell line having accession number KCTC 13095BP, wherein a SCN5A gene consisting of NCBI accession no. NM_198056 encoding Nav1.5 and a puromycin selection marker are inserted into a chromosome of the cell.

2. The cell line of claim 1, wherein the cell is a human embryonic kidney 293 (HEK293) cell, and the cell line has sodium current magnitude in a range from about 5.5 nA to about 19.6 nA.

3. The cell line of claim 2, wherein the cell line has average sodium current quantity of about 8.8±0.8 nA.

4. A method of measuring cardiotoxicity of a test substance, the method comprising:
  (1) contacting a test substance to the cell line of claim 1; and
  (2) measuring the magnitude of the voltage-gated sodium channel Nav1.5 in the cell line in contact with the test substance.

5. A method of screening an inhibitor for cardiotoxicity, the method comprising:
  (1) contacting a test substance to the cell line of claim 1;
  (2) measuring the magnitude of the voltage-gated sodium channel Nav1.5 in the cell line in contact with the test substance; and
  (3) selecting the test substance having an increased magnitude of Nav1.5 current as compared to the magnitude of Nav1.5 current in a control sample.

* * * * *